United States Patent [19]

Tsaur et al.

[11] Patent Number: 5,441,728
[45] Date of Patent: Aug. 15, 1995

[54] HAIRSPRAY COMPOSITIONS

[75] Inventors: Liang S. Tsaur, Norwood, N.J.; Michael P. Aronson, West Nyack, N.Y.; Frank Jones, Orange; G. Jae Lee, Trumbull, both of Conn.

[73] Assignee: Chesebrough-Pond's USA Co., a division of Conopco, Inc., Greenwich, Conn.

[21] Appl. No.: 263,849

[22] Filed: Jun. 22, 1994

[51] Int. Cl.⁶ ............................................. A61K 7/11
[52] U.S. Cl. .................. 424/70.11; 424/47; 424/DIG. 1; 424/DIG. 2; 424/70.16; 424/70.2; 132/210
[58] Field of Search ............ 424/71, 70, 45, DIG. 1, 424/DIG. 2, 47, 70.2, 70.11, 70.16, 78.02; 514/957; 132/210

[56] References Cited

U.S. PATENT DOCUMENTS

| | | | |
|---|---|---|---|
| 3,800,033 | 3/1974 | Flawn et al. | 424/71 |
| 3,927,199 | 12/1975 | Micchelli et al. | 424/71 |
| 4,173,627 | 11/1979 | Madrange nee Dermain | 424/71 |
| 4,300,580 | 11/1981 | O'Neill et al. | 424/47 |
| 4,402,977 | 9/1983 | Grollier et al. | 424/71 |
| 4,525,524 | 6/1985 | Tung et al. | 424/71 |
| 4,859,455 | 8/1989 | Nowak, Jr. et al. | 424/71 |
| 4,871,529 | 10/1989 | Sramek | 424/47 |
| 4,874,604 | 10/1989 | Sramek | 424/47 |
| 4,983,383 | 1/1991 | Maksimoski et al. | 424/47 |
| 4,983,418 | 1/1991 | Murphy et al. | 424/47 |
| 4,985,239 | 1/1991 | Yahagi et al. | 424/71 |
| 5,021,238 | 6/1991 | Martino et al. | 424/47 |
| 5,068,099 | 11/1991 | Sramek | 424/47 |
| 5,094,838 | 3/1992 | Benson et al. | 424/47 |
| 5,126,126 | 6/1992 | Varaprath et al. | 424/71 |
| 5,158,762 | 10/1992 | Pierce | 424/47 |
| 5,160,729 | 11/1992 | Login et al. | 424/47 |
| 5,164,177 | 11/1992 | Bhatt et al. | 424/47 |
| 5,182,098 | 1/1993 | Kopolow et al. | 424/47 |
| 5,208,295 | 5/1993 | Chaudhuri et al. | 525/327.6 |
| 5,266,303 | 11/1993 | Myers et al. | 424/47 |
| 5,266,308 | 11/1993 | Lee et al. | 424/71 |

FOREIGN PATENT DOCUMENTS

| | | | |
|---|---|---|---|
| 1222461 | 6/1987 | Canada. | |
| 331994 | 9/1989 | European Pat. Off. | 424/71 |
| 551748 | 7/1993 | European Pat. Off. | 424/71 |
| 0590604 | 4/1994 | European Pat. Off. | |
| 2098624 | 11/1982 | United Kingdom. | |

OTHER PUBLICATIONS

Oteri, et al. (1991). Cosmetics & Toiletries, vol. 106, pp. 29–34.

*Primary Examiner*—Raj Bawa
*Attorney, Agent, or Firm*—Milton L. Honig

[57] ABSTRACT

An aqueous hair treatment composition is provided that includes a water-soluble polymer having a solution viscosity at 10% in water of less than about 20,000 cps at 25° C., and a latex of water-insoluble polymeric particles dispersed in water and having a glass transition temperature between 250 and 300° K., the average particle size being no higher than about 3 microns. Preferably the latex particles are formed from respective monomers by emulsion polymerization.

12 Claims, No Drawings

HAIRSPRAY COMPOSITIONS

BACKGROUND OF THE INVENTION

1. Field of the Invention

The invention relates to hairspray compositions especially formulated for use in low organic volatile systems.

2. Related Art

Hairspray compositions must meet a number of functional requirements. These include good holding ability and curl retention without giving a harsh, brittle feeling to the hair. Even under humid conditions there must be good hold and curl retention. Another requirement is that the hairspray be capable of being removed upon washing the hair at the time of shampooing. Additionally, the compositions must include the properties of low stickiness and a lack of powdering or flaking.

Various resins have been employed in hairspray compositions to achieve the aforementioned desirable properties. Illustrative of such resins are the copolymers of vinylpyrrolidone with vinyl acetate, available commercially under such trademarks as Luviskol VA 73 by the BASF Corporation and homopolymers of vinylpyrrolidone commercialized under the trademark PVP K-30 by ISP Corporation. Typical of this art are disclosures in U.S. Pat. No. 3,800,033 (Flawn et al) and U.S. Pat. No. 4,173,627 (Madrange nee Dermain et al). A higher molecular weight homopolymer of vinylpyrrolidone, PVP K-90 Resin trademark of ISP Corporation, is disclosed in U.S. Pat. No. 4,874,604 (Sramek). The aforementioned polymeric resins are of the nonionic variety.

Amphoteric resins have also been extensively employed. These polymers contain cationic radicals derived from monomers such as t-butyl aminoethyl methacrylate as well as carboxyl radicals derived from monomers such as acrylic acid or methacrylic acid. Representative of this group is a product manufactured by the National Starch and Chemical Corporation under the trademark Amphomer identified on product labels by the CTFA name of Octylacrylamide/Acrylates/-Butylaminoethyl Methacrylate Copolymers. Use of Amphomer alone or in conjunction with other resins for hairsprays has been reported in U.S. Pat. No. 3,927,199 (Micchelli et al), U.S. Pat. No. 4,402,977 (Grollier et al), U.S. Pat. No. 4,859,455 (Nowak, Jr. et al), U.S. Pat. No. 4,871,529 (Sramek), U.S. Pat. No. 4,983,383 (Maksimoski et al), U.S. Pat. No. 4,983,418 (Murphy et al), U.S. Pat. No. 5,021,238 (Martino et al), GB 2 098 624 (Madrange) and Canadian Patent 1 222 461 (Varco).

Anionic polymeric resins have also been utilized in this art. For instance, U.S. Pat. No. 4,300,580 (O'Neill et al) discloses linear polyesters prepared from isophthalic acid, the sodium salt of 5-sulfoisophthalic acid and diethylene glycol. Eastman AQ Polymers for water-dispersed hairsprays are based on this technology. Other polyester and sulfo substituted polymer systems are described in U.S. Pat. No. 4,525,524 (Tung et al).

Environmental concerns and legislation addressing such concerns have required product reformulations to meet these challenges. Organic solvent-based sprays must, at least in part, now be substituted by water systems. Concentrations of organic propellants present in these water systems must also be adjusted to relatively low levels. With these constraints, certain problems have arisen. Water-dispersed systems are slow to dry. Not only do they result in wetness on the hair but there is also an undesirable coolness sensation that imparts a chill. Quite significantly there is also difficulty in developing the style. Resins formulated in a water-dispersed system can have weak holding power.

Some systems such as the Eastman AQ Resins have good setting or holding but removability from hair is quite poor because these resins are not water soluble.

Furthermore, there is the problem of providing a uniform spray particle size with water-dispersed resins. A still further problem is that of improving glossiness to counteract resins that usually tend to dull hair.

Recently there has been disclosed in a U.S. Pat. No. 5,068,099 (Sramek) an aerosol hairspray package claiming reduced volatile organic compound emission during the useful life of the package. The spray composition contains a combination of at least two polymers differing in weight average molecular weight by at least 1.5. This blend of polymers combines with a low delivery rate discharge mechanism to provide an atomized composition with mean particle size of at least 60 average microns. A significant drawback of this technology is the necessity for very substantial amounts of volatile alcohol; water is present at levels no higher than 10% by weight. Instead of eliminating volatiles from the formula, the patent merely controls the spray emission thereof. Unfortunately, at some point in the life cycle of the package, volatiles will be emitted into the atmosphere. A further problem with this system is the relatively low rate of spray. It would be desirable to utilize systems with much higher spray rates.

Accordingly, it is an object of the present invention to provide a hairspray suitable for water-based systems having improved holding and styling characteristics.

Another object of the present invention is to provide a hairspray composition based on a water-based system that dries fairly quickly and does not impart an undue wetness or cool feel to hair or scalp.

A further object of the present invention is to provide a hairspray composition for water-based systems that improves glossiness of the hair.

A still further object of the present invention is to provide a hairspray composition for water-based systems that can be sprayed as relatively uniform particles.

These and other objects of the present invention will become more evident from the following summary and detailed description.

SUMMARY OF THE INVENTION

An aqueous hairspray composition is provided including:

(i) a water-soluble polymer having a solution viscosity at 10% in water of less than about 20,000 cps at 25° C., the polymer being present in an effective amount for setting hair; and (ii) a latex of water-insoluble polymeric particles dispersed in water, the average particle size being no higher than about 3 microns, the particles having a glass transition temperature from 250 to 300° K. and being present in an effective amount to interact with the polymer to further improve the setting of hair.

In a further aspect of the invention, a method for setting hair is also provided wherein the water-soluble polymer and the latex of water-insoluble polymeric particles are applied to the hair, preferably through spray application.

Hairspray compositions of this invention are dispersed in water which may contain from 0–50% of a propellant such as dimethyl ether.

DETAILED DESCRIPTION

It has been discovered that many of the objects of the present invention can be achieved through a hair treatment composition that includes a water-soluble polymer having a solution viscosity of less than about 20,000 cps at 25° C. when 10% of polymer is placed in water, and a latex of water-insoluble polymeric particles with a glass transition temperature in the range of 250 to 300° K. The latex and water-soluble polymer interact with one another to provide an overall superior hairsetting composition.

According to the invention a wide variety of water-soluble polymers are suitable for use in the composition. These polymers should have a viscosity of less than about 20,000 cps at 25° C. when 10% is placed in water, more preferably a viscosity of less than about 10,000 cps. The amount of the polymer may range from about 1 to 30%, preferably from about 1.5 to 10% by weight of the hairspray composition.

The water-soluble polymer may be selected from nonionic, anionic, cationic or amphoteric type hair fixative polymers. However, in systems where the latex particles are anionic, the water-soluble polymer should not be cationic so as to avoid clumping.

Examples of anionic hair fixative polymers are the copolymers of vinyl acetate and crotonic acid, terpolymers of vinyl acetate, crotonic acid and a vinyl ester of an alpha-branched saturated aliphatic monocarboxylic acid such as vinyl neodecanoate; copolymers of methyl vinyl ether and maleic anhydride (molar ratio about 1.1) wherein such copolymers are 50% esterified with a saturated alcohol containing from 1 to 4 carbon atoms such as ethanol or butanol; and acrylic copolymers, terpolymers, etc., containing acrylic acid or methacrylic acid as the anionic radical-containing moiety and esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the emulsion polymerized terpolymer of methacrylic acid, n-butyl acrylate and ethyl acrylate (e.g., in a weight percent ratio of 1:42:27, respectively). Another specific example is Ultrahold ® 8 (CTFA-Cosmetic, Toiletries and Fragrance Association-designation of Acrylate/Acrylamide Copolymer).

Amphoteric polymers which can contain cationic groups derived from monomers such as tobutyl aminoethyl methacrylate as well as carboxyl groups derived from monomers such as acrylic acid or methacrylic acid can also be used in the present invention. One specific example of an amphoteric hair fixative polymer is Amphomer ® sold by the National Starch and Chemical Corporation.

Examples of nonionic hair fixative polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 sold by ISP (formerly GAF Corporation) under the tradename PVP K-90 and those having an average molecular weight of about 1,000,000 sold under the trademark of PVP K-120.

Examples of cationic hair fixative polymers are copolymers of amino-functional acrylate monomers such as lower alkylaminoalkyl acrylate or methacrylate monomers such as dimethylaminoethyl methacrylate with compatible monomers such N-vinylpyrrolidone, vinyl caprolactam, or alkyl methacrylates such as methyl methacrylate and ethyl methacrylate and alkyl acrylates such as ethyl acrylate and n-butyl acrylate. Cationic hair fixative polymers containing N-vinylpyrrolidone are commercially available from ISP Corporation such as those sold under the trademarks of Copolymer 845 and Copolymer 937 (copolymers of N-vinylpyrrolidone and t-butylaminoethyl methacrylate of average molecular weight about 1,000,000) and Gafquat ® 755 and 755N (quaternary ammonium polymers formed by the reaction of dimethyl sulfate and a copolymer of N-vinylpyrrolidone and dimethylaminoethyl methacrylate of average molecular weight about 1,000,000).

According to the present invention there is also required a latex of water-insoluble polymeric particles dispersed in water. Amounts of the particles may range from about 1 to about 30%, preferably from about 1.5 to about 10% by weight of the hairspray composition. The average particle size should be no higher than 3 microns, preferably no higher than 1 micron, optimally less than 1 micron. A preferred average diameter size ranges from 0.005 to 1 micron. Finally and most important, is that the polymeric particles have a glass transition temperature that lies between 250 and 300° K.

A wide variety of homopolymers and copolymers are suitable in forming the latex particles. Vinyl polymerization derived polymers are preferred rather than condensation polymers (e.g. Eastman AQ type). Monomers which comprise the polymers may be selected from any emulsion polymerizable monomer that contains ethylenically unsaturated groups such as α-methylstyrene, divinylbenzene, styrene, $C_1$–$C_{20}$ esters of acrylic acid, methacrylic acid, acrylamide, methacrylamide, crotonic acid or maleic acid, vinyl acetate, vinyl neodecanoate and combinations of these. Preferred latices are those of styrene/butyl acrylate, methyl methacrylate/butyl acrylate, vinyl acetate/butyl acrylate and vinyl acetate/methyl methacrylate.

A variety of techniques well-known in the art can be used to prepare the latex of water-insoluble polymer particles useful in the present invention. These include batch, semi-continuous and seeded emulsion polymerization (Encyclopedia of Polymer Science and Engineering, Volume 6, 1990).

In a preferred aspect of the present invention, the latex particles are formed by emulsion polymerizing monomers constituting the latex in aqueous media. For purposes of this invention, the term "resin" will mean the aforementioned preferred aspect of the combined latex particles and water-soluble polymer.

Solids content of the latex may range anywhere from about 5 to 60%, preferably 20 to 50%. The ratio of water-soluble polymer to latex particles may range anywhere from about 10:1 to about 1:10 preferably from about 7:3 to about 3:7, optimally from about 2:1 to 1:2 by weight.

The term "water-soluble" refers to any material that has solubility of at least 5 gram per 100 grams of water, i.e. 5%, preferably a solubility of at least 10% by weight. Conversely, the term "water-insoluble" refers to substances that are insoluble at a level of less than 0.1 gram per 100 grams of water, i.e. less than 0.1% by weight.

Compositions of the present invention will also include water as a solvent carrier for the polymers and other components. Water will be present in amounts ranging from about 20% to about 99%, preferably from about 40% to about 95% by weight. Optimally, water will be the major if not exclusive solvent, i.e. liquid carrier, for the hair treatment compositions of this invention. Volatile organic solvents such as methanol, ethanol or isopropanol are preferably absent.

With certain of the resins it may be necessary to neutralize some acidic groups to promote solubility/dispersibility. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). Amounts of the neutralizing agents will range from about 0.001 to about 10% by weight.

The present hair treatment compositions may be formulated as sprays in aerosol or nonaerosol forms. If an aerosol hairspray is desired, a propellant must be included in the composition. This agent is responsible for expelling the other materials from the container and forming the hairspray character.

The propellant gas can be any liquefiable gas conventionally used for aerosol containers. Preferably the density of the propellant or mixture thereof is less than the hairspray concentrate so that pure propellant is not emitted from the container. Examples of suitable propellants include dimethyl ether, propane, n-butane and isobutane, used singly or admixed. Dimethyl ether is preferred because of its water-solubility up to 35% by weight.

The amount of the propellant gases is governed by normal factors well known in the aerosol art. For hairsprays the level of propellant is generally from about 3 to about 50%, preferably from about 5 to about 45%, optimally about 30% of the total composition.

Small quantities of surfactant ranging anywhere from 0.1 to about 10%, preferably from about 0.1 to about 1%, optimally about 0.3% by weight may be present in the compositions of the invention. The surfactant may be an anionic, nonionic or cationic emulsifier. Particularly preferred are nonionic emulsifiers which are formed from alkoxylation of hydrophobes such as fatty alcohols, fatty acids and phenols. Illustrative of such material is Triton X-100, and isooctyl phenyl polyethoxyethanol.

Resins when deposited upon hair quite often impart dullness. Counteraction of the dullness effect may be achieved by incorporating low levels of $C_{10}$–$C_{20}$ fatty alcohol esters. Particularly preferred is cetearyl octanoate. Amounts of these luster imparting agents will range from about 0.001 to about 1%, preferably from about 0.01 to about 0.5%, optimally from about 0.02 to about 0.1% by weight.

Compositions of this invention may contain any other ingredient normally used in hairsprays. These other ingredients may include antifoam agents, proteins, antioxidants, fragrances, antimicrobials and sunscreens. Each of these ingredients will be present in an amount effective to accomplish its purpose.

Hairspray formulations of the present invention may, if desired, be packaged in a pump spray container operated without any propellant. Otherwise, the composition may be charged into a suitable pressurizable container which is sealed and then charged with propellant according to conventional techniques.

The following examples will more fully illustrate the embodiments of this invention. All pans, percentages and proportions referred to herein and the appended claims are by weight unless otherwise indicated.

EXAMPLES 1-3

Preparation of Latex Resins Based on Styrene/Butylacrylate Latex

Examples 1 to 3 with the latex resin composition as shown in Table I were prepared as follows: 120 grams (360 grams for Example 3) of deionized water, all the Amphomer LV71 and AMP (aminomethylpropanol) as shown in Table I were added to a 4-neck round bottom glass reactor equipped with temperature controller, nitrogen inlet and outlet, mechanical stirrer and condenser. The reactor was purged with nitrogen gas, heated and maintained at 80° C. to dissolve all the Amphomer LV71. Three grams of monomer mixture were charged to the reactor and then 10 grams of 1% potassium persulfate solution were added to start the polymerization. Five minutes after adding the persulfate solution, the remaining monomer mixture was fed to the reactor over a 15 minute period. Thereupon the reaction was maintained at 80° C. for another 50 minutes. The emulsion was cooled to room temperature and filtered through a 25 micrometer filter. Particle size, pH, emulsion viscosity and film formation properties were measured and recorded in Table I.

TABLE I

| | EXAMPLE 1 | EXAMPLE 2 | EXAMPLE 3 |
|---|---|---|---|
| Amphomer LV71 | 10 g | 10 g | 30 g |
| AMP | 1.2 g | 1.2 g | 3.6 g |
| Latex Monomer Mixture | | | |
| Styrene | 10 g | 4 g | 12 g |
| Butylacrylate | — | 6 g | 18 g |
| Particle Size | 134 nm | 81 nm | 85 nm |
| pH | 6.5 | 6.6 | 6.8 |
| Viscosity* (30 rpm, 11% solid, #1 spindle) | 6 cps | 6 cps | 7.5 cps |
| Film Formation at room temperature | No | Yes | Yes |

*The viscosity of Amphomer LV71 at 11% solid is 12 cps (with LVT #1 spindle at rpm, 30 sec. reading).

Film "hardness or formation", a measure of hair hold capability, was evaluated by evenly applying 2–4 grams of concentrate onto an 8"×8" glass plate. Samples were allowed to dry overnight to achieve a thick, dry film. Observations of gelling of the film were recorded. Using a sharp-pointed tool, the film was lightly "scratched" upon the glass plate. Observations were then recorded with regard to hardness and brittleness.

EXAMPLES 4–6

Evaluation of Latex Resins Based on Styrene/Butylacrylate Latex in Zero VOC Hair Spray Formulation Film "rinseability" was evaluated by placing a clean, dry, 8"×8" glass plate in a fume hood. The sample hairspray was then applied for 10 seconds evenly coating the glass plate throughout. After drying at least 1 hour at room temperature, a visual observation of clarity, color precipitate or separation, and brittle-cracks in the film were noted. A few drops of warm tap water (about 100° F.) were lightly applied onto the plate. Through light finger action the film was caused to lightly dissolve. Texture was noted. A ranking for the samples was then performed according to ease of rinsability (very poor, poor, medium, good, very good) in comparison to available controls.

Due to its poor film forming properties, the latex resin of Example 1 was not evaluated for hair spray application. Examples 2 and 3 were formulated in a water-based hair spray formula with the composition shown in Table IIA. Amphomer LV71 was used as the control (Example 6). All these three water-based formulas contain 5.5% polymer solid. Properties and performance of these hairspray formulas were evaluated and are summarized in Table IIB. The data clearly shows that the latex resin of this invention has much better hair fixative properties than the water-soluble polymer alone.

TABLE IIA

|  | Example 4 | Example 5 | Example 6 |
| --- | --- | --- | --- |
| D.I. Water | 49.02% | 73.07% | 49.02% |
| Latex Resin | 50.25% | 26.2% | 50.25% |
|  | Ex. 2 (11%) | Ex. 3 (21.1%) | Amphomer LV71 (11%) |
| D.C. 190 ® Surfactant | 0.10% | 0.10% | 0.10% |
| Methyl Paraben | 0.20% | 0.20% | 0.20% |
| Glydant | 0.05% | 0.05% | 0.05% |
| Triton X-100 | 0.20% | 0.20% | 0.20% |
| Cetearyl Octanoate | 0.03% | 0.03% | 0.03% |
| Fragrance | 0.15% | 0.15% | 0.15% |
| TOTAL | 100% | 100% | 100% |

TABLE IIB

|  | Performance | | |
| --- | --- | --- | --- |
|  | Example 4 | Example 5 | Example 6 |
| Curl Strength (g-cm) | 8.4 ± 1.1 | 6.0 ± 0.8 | 4.7 ± 1.0 |
| Curl Retention | | | |
| 15 minutes | 83.7% | 86.9% | 79.9% |
| 30 minutes | 75.5% | 78.3% | 70.8% |
| 1 hour | 71.6% | 74.5% | 61.7% |
| 2 hours | 67.1% | 71.2% | 53.6% |
| 4 hours | 65.2% | 68.7% | 49.7% |
| Overnight | 60.4% | 64.3% | 47.3% |
| Rinseability | Very Good | Very Good | Very Good |

EXAMPLES 7–9

Preparation of Latex Resins Based on Methylmethacrylate/Butylacrylate Latex

The compositions for these Examples are shown in Table III. These compositions include the same monomers (methylmethacrylate/butylacrylate) but have different ratios of Amphomer LV71 (water-soluble polymer) to monomer (hydrophobic emulsion polymer). Preparation is similar to that used for Example 3. A reactor was charged with 290 grams of deionized water, all the Amphomer LV71 and AMP. The solution was heated and maintained at 80° C. to dissolve the Amphomer LV71 under a slow stream of nitrogen gas. After dissolving all the Amphomer LV71, five grams of monomer mixture and 10 grams of 1.2% potassium persulfate solution were added to the reactor to start the polymerization reaction. Five minutes after adding the persulfate solution, the remaining monomer mixture was fed to the reactor over a span of 15 minutes. The reaction was held at 80° C. for another 60 minutes. Upon cooling to room temperature, the emulsion was filtered through a 25 micrometer filter for further evaluation. Particle size, pH, emulsion viscosity and film formation properties were determined and are reported in Table III.

TABLE III

|  | EXAMPLE 7 | EXAMPLE 8 | EXAMPLE 9 |
| --- | --- | --- | --- |
| Amphomer LV71 | 26.7 g | 40.0 g | 53.3 g |
| AMP (aminomethyl-propanol) | 3.2 g | 4.8 g | 6.4 g |
| Latex Monomer Mixture | | | |
| Methylmethacrylate | 21.3 g | 16 g | 10.7 g |
| Butylacrylate | 32 g | 24 g | 16 g |
| % Solid | 21.1% | 20.8% | 21.6% |
| Particle Size | 162 nm | 66 nm | 48 nm |
| Viscosity (30 rpm) | 66 cps | 82 cps | 3100 cps |
| pH | 6.7 | 6.7 | 6.7 |
| Film Formation at room temperature | Yes | Yes | Yes |

EXAMPLES 10–13

Hairspray Formulations Containing Latex Resin Based on Methylacrylate/Butylacrylate Latex Latex resins of Examples 7 to 9 were formulated in water-based aerosol and pump hairspray compositions. Physical properties and performance of these formulations were evaluated by in-vitro tests. Two alcohol-based hairspray formulas, Examples 13A and 13B were used as controls. Compositions of the two alcohol-based products are given in Table VI. The composition, properties and performance of aerosol and pump formulations are summarized in Tables IV and V, respectively.

TABLE IV

| Water-Based Aerosol airspray | | | | |
| --- | --- | --- | --- | --- |
|  | Example 10 | Example 11 | Example 12 | Example 13A* |
| Formulation | | | | |
| D.I. Water | 44.6% | 44.5% | 44.6% | Alcohol-based Hairspray (Control) |
| Latex Resin | 25.0% | 25.1% | 25.0% | |
|  | Example 7 | Example 8 | Example 9 | |
| D.C. 190 ® Surfactant | 0.07% | 0.07% | 0.07% | |
| Triton X-100 | 0.21% | 0.21% | 0.21% | |
| Cetearyl Octanoate | 0.02% | 0.02% | 0.02% | |
| Fragrance | 0.10% | 0.10% | 0.10% | |
| Dimethylether | 30.0% | 30.0% | 30.0% | |
| TOTAL | 100% | 100% | 100% | |
| Physical Properties | | | | |
| pH | 6.70 | 6.75 | 6.70 | |
| Viscosity (Cps) | 4.5 | 5.0 | 4.5 | |
| Performance | | | | |
| Hair holding | Very Good | Very Good | Very Good | Very Good |
| Rinseability | Very Good | Very Good | Very Good | Very Good |
| Gloss | Very | Very | Poor | Very |

TABLE IV-continued

Water-Based Aerosol airspray

| | Example 10 | Example 11 | Example 12 | Example 13A* |
|---|---|---|---|---|
| | Good | Good | Good | |

*See Table VII for composition.

TABLE V

Water-Based Pump Hairspray

| | Example 10 | Example 11 | Example 12 | Example 13B* |
|---|---|---|---|---|
| Formulation | | | | |
| D.I. Water | 73.07% | 72.97% | 73.2% | Alcohol-based Hairspray (Control) |
| Latex Resin | 26.2% Example 7 | 26.3% Example 8 | 26.1% Example 9 | |
| D.C. 190 ® Surfactant | 0.10% | 0.10% | 0.10% | |
| Methyl paraben | 0.20% | 0.20% | 0.20% | |
| Glydant | 0.05% | 0.05% | 0.05% | |
| Triton X-100 | 0.20% | 0.20% | 0.20% | |
| Cetearyl Octanoate | 0.03% | 0.03% | 0.03% | |
| Fragrance | 0.15% | 0.15% | 0.15% | |
| TOTAL | 100% | 100% | 100% | |
| Physical Properties | | | | |
| pH | 6.75 | 6.6 | 6.6 | |
| Viscosity (Cps) | 4.2 | 4.0 | 4.0 | |
| Performance | | | | |
| Hair holding | Excellent | Very Good | Good | Very Good |
| Rinseability | Poor | Very Good | Very Good | Very Good |
| Gloss | Good | Very Good | Good | Good |

*See Table VII for composition.

| INGREDIENT | % BY WEIGHT |
|---|---|
| EXAMPLE 13A | |
| Ethyl Alcohol (SDA 40) | 74.99 |
| Aminomethylpropanol | 0.39 |
| NSC Resin 28-2930 | 4.50 |
| Fragrance | 0.12 |
| Propellant 50 (Hydrocarbon) | 20.00 |
| EXAMPLE 13B | |
| Ethyl Alcohol (SDA 40) | 77.096 |
| D.I. Water | 16.251 |
| Amphomer 28-4910 | 5.600 |
| Aminomethylpropanol | 1.023 |
| Fragrance | 0.030 |

EXAMPLES 14 to 17

Four latex resin compositions with components shown in Table VII were prepared by the same procedure as that used in Examples 7-9. All the latex resin compositions have the same ratio of Amphomer LV71 to monomer mixture but different monomer compositions. These latex resin compositions, except for Example 16 (which had poor film forming properties), were formulated in a water-based aerosol and pump hairspray with the same formulation as shown in Table IV and V, respectively. These compositions were evaluated for hairspray performance. Results are summarized in Table VII. The latex resin of Example 8 was used for comparison.

TABLE VII

| | Example 14 | Example 8 | Example 15 | Example 16 | Example 17 |
|---|---|---|---|---|---|
| Latex Resin Composition and Properties | | | | | |
| Amphomer LV71 | 40 g | 40 g | 40 g | 40 g | 40 g |
| Methylmethacrylate | 12 g | 16 g | 28 g | 0 g | 0 g |
| Butylacrylate | 28 9 | 24 g | 12 g | 0 g | 8 g |
| Vinylacetate | 0 g | 0 g | 0 g | 40 g | 32 g |
| % Solid | 21% | 20.8% | 21.1% | 19.6% | 19.8% |
| pH | 6.7 | 6.7 | 6.7 | 6.2 | 6.4 |
| Particle Size | 81 nm | 66 nm | 72 nm | 77 nm | 67 nm |
| Viscosity (Cps) | 330 | 82 | 114 | 7 | 8 |
| Film Formation at room temperature | Yes | Yes | Yes | No | Yes |
| Properties and Performance of Aerosol Hairspray | | | | | |
| pH | 6.65 | 6.75 | 6.4 | — | 6.4 |
| Viscosity (Cps) | 4.5 | 5.0 | 5.0 | — | 3.5 |
| Hair holding | Very Good | Very Good | Very Good | — | Poor |
| Rinseability | Very Good | Very Good | Very Good | — | Very Good |
| Gloss | Poor | Good | Very Good | — | Very Good |
| Properties and Performance of Pump Hairspray | | | | | |
| pH | 6.6 | 6.6 | 6.8 | — | 6.45 |
| Viscosity (Cps) | 4.0 | 4.0 | 4.5 | — | 3.5 |
| Hair holding | Very Good | Very Good | Poor | — | Very Good |
| Rinseability | Good | Very Good | Very Good | — | Very Good |
| Gloss | Good | Very Good | Good | — | Very Good |

EXAMPLES 18-24

Specifications

The compositions of these Examples are shown in Table VIII. These resins were prepared by adding 280 grams (180 grams for Examples 18 and 24) of deionized water, 0.6 grams sodium lauryl sulfate (1.0 grams for Examples 18 and 24) and 1.0 grams surfactant combination and 1.2 grams AMP (Examples 19-21; 2.4 grams AMP in Example 23) to a 4-neck round bottom glass reactor. The reactor was purged with nitrogen gas, heated and maintained at 80° C. to dissolve all the surfactant and water-soluble polymer. Ten grams of the acrylate monomers were added to the reactor followed by 20 grams of 1% potassium persulfate solution to start the polymerization. Five minutes later, the remaining monomer mixture was fed to the reactor over a 40minute period. Thereupon, the reactants were heated at 80° C. for another 50 minutes. The resultant emulsion was cooled to room temperature and the pH adjusted to 6.0 to 7.0 by neutralization with aminomethylpropanol. Part of the emulsion was physically blended with Amphomer LV71 solution (16 weight%) according to the amounts shown in Table VIII (second section) to achieve the final latex resin composition.

The final latex resin compositions were then incorporated into a hair setting composition that included an aerosol propellant. These formulas are outlined in Tables IX and X.

TABLE VIII

| | EXAMPLE (WEIGHT %) | | | | | | |
|---|---|---|---|---|---|---|---|
| | 18 | 19 | 20 | 21 | 22 | 23 | 24 |
| Latex Resin | | | | | | | |
| Amphomer LV71 | — | 10 | 10 | 10 | — | 20 | — |
| Polyvinylalcohol | — | — | — | — | 10 | — | — |
| Butylacrylate | 56 | 54 | 54 | 54 | 54 | 48 | 60 |
| Methylmethacrylate | 38 | 36 | 36 | 36 | 36 | 32 | 40 |
| Methacrylic Acid | 6 | — | — | — | — | — | — |

TABLE VIII-continued

| | EXAMPLE (WEIGHT %) | | | | | | |
|---|---|---|---|---|---|---|---|
| | 18 | 19 | 20 | 21 | 22 | 23 | 24 |
| Physical Blending of Latex Resin with Water-Soluble Polymer | | | | | | | |
| Latex Resin | 50 | 100 | 78 | 56 | 55 | 63 | * |
| Amphomer LV71 | 50 | 0 | 22 | 44 | 45 | 37 | |
| Final Latex Resin Composition | | | | | | | |
| Amphomer LV71 | 50 | 10 | 30 | 50 | 45 | 50 | |
| Polyvinylalcohol | — | — | — | — | 5.0 | — | |
| Butlyacrylate | 28 | 54 | 42 | 30 | 30 | 30 | |
| Methylmethacrylate | 19 | 36 | 28 | 20 | 20 | 20 | |
| Methacrylic Acid | 3 | — | — | — | — | — | |

*Coagulate

EXAMPLES 25–27

Preparation of Polymer Latexes

Polymer latexes of examples 25 to 27 with the composition as shown in Table XI were prepared as follows: 200 grams of deionized water, 12.5 grams of Rhone-Poulenc Igepal CO-880 and 0.5 grams of sodium lauryl sulfate were added to a 500 ml reactor. The reactor was purged with nitrogen and heated and maintained at 63° C. Then, 10 grams of monomer were charged to the reactor and 50 grams of 1.2 wt % of potassium persulfate solution was added to start the polymerization reaction. Five minutes after adding the initiator solution, the remaining monomer was fed to the reactor over a period of 2 hours. The reaction was continued

TABLE IX

| COMPONENTS | LATEX RESIN COMPOSITION EXAMPLES | | | | | | ALCOHOL BASE Control |
|---|---|---|---|---|---|---|---|
| | 18 | 19 | 20 | 21 | 22 | 23 | |
| Pump Hairspray Formulations, Properties and Performance (5.5% resin) | | | | | | | |
| Water. D.I. | 73.77 | 74.97 | 73.67 | 71.07 | 70.47 | 72.87 | |
| Latex Resin Composition % (includes water) | 25.50 | 24.30 | 25.60 | 28.20 | 28.80 | 26.40 | |
| Methyl Paraben | 0.20 | 0.20 | 0.20 | 0.20 | 0.20 | 0.20 | |
| Triton X-100 | 0.20 | 0.20 | 0.20 | 0.20 | 0.20 | 0.20 | |
| Fragrance | 0.15 | 0.15 | 0.15 | 0.15 | 0.15 | 0.15 | |
| DC-190 ® Surfactant | 0.10 | 0.10 | 0.10 | 0.10 | 0.10 | 0.10 | |
| Glydant | 0.05 | 0.05 | 0.05 | 0.05 | 0.05 | 0.05 | |
| Cetearyl Octanoate | 0.03 | 0.03 | 0.03 | 0.03 | 0.03 | 0.03 | |
| TOTAL | 100% | 100% | 100% | 100% | 100% | 100% | |
| Physical Property | | | | | | | |
| pH | 6.46 | 6.72 | 6.53 | 6.51 | 6.52 | 6.57 | |
| Viscosity (Cps) | 4.0 | 3.5 | 4.0 | 4.0 | 4.0 | 4.5 | |
| Performance | | | | | | | |
| Hair Hold Capability | Good | Good | Fair | Good | Very Good | Very Good | Very Good |
| Film Characteristics | Clear/Hard | Milky/Soft | Clear/Hard | Clear/Hard | Clear/Hard | Clear/Hard | Clear/Hard |
| Rinseability | Very Good | Good/Fair | Very Good | Very Good | Very Good | Very Good | Very Good |
| Gloss | Good | S/Dull | S/Dull | Good | Very Good | Good | Very Good |

TABLE X

| COMPONENTS | LATEX RESIN COMPOSITION EXAMPLES | | | | | | ALCOHOL BASE Control |
|---|---|---|---|---|---|---|---|
| | 18 | 19 | 20 | 21 | 22 | 23 | |
| Aerosol Hairspray Formulations, Properties and Performance (5.25% resin) | | | | | | | |
| Water, D.I. | 45.09 | 46.35 | 45.09 | 42.64 | 42.08 | 44.46 | |
| Latex Resin Composition % (includes water) | 24.50 | 23.24 | 24.50 | 26.95 | 27.51 | 25.13 | |
| Dimethylether | 30.00 | 30.00 | 30.00 | 30.00 | 30.00 | 30.00 | |
| Triton X-100 | 0.21 | 0.21 | 0.21 | 0.21 | 0.21 | 0.21 | |
| Fragrance | 0.10 | 0.10 | 0.10 | 0.10 | 0.10 | 0.10 | |
| DC-190 ® Surfactant | 0.07 | 0.07 | 0.07 | 0.07 | 0.07 | 0.07 | |
| Cetearyl Octanoate | 0.02 | 0.02 | 0.02 | 0.02 | 0.02 | 0.02 | |
| TOTAL | 100% | 100% | 100% | 100% | 100% | 100% | |
| Physical Properties | | | | | | | |
| pH | 6.40 | 6.66 | 6.53 | 6.42 | 6.42 | 6.47 | |
| Viscosity (Cps) | 4.5 | 4.5 | 4.5 | 4.5 | 4.5 | 5.5 | |
| Performance | | | | | | | |
| Hair Hold Capability | Good | Good | Poor | Very Good | Good/Fair | Good | Very Good |
| Film Characteristics | Clear/Hard | Milky/Hard | Milky/Soft | Clear/Hard | Clear/Soft | Clear/Hard | Clear/Hard |
| Rinseability | Very Good | Good/Poor | Very Good | Very Good | Very Good | Very Good | Very Good |
| Gloss | Good | Good | Dull | Very Good | Good | Good | Very Good | for another 3 hours at 63° C. The latex was then cooled and saved for formulation.

TABLE XI

|  | EXAMPLE 25 | EXAMPLE 26 | EXAMPLE 27 |
|---|---|---|---|
| Water | 200 g | 200 g | 200 g |
| Igepal CO-880 | 12.5 g | 12.5 g | 12.5 g |
| NaLS | 0.5 g | 0.5 g | 0.5 g |
| Monomer |  |  |  |
| Styrene | 62.5 g | — | — |
| MMA* | — | 62.5 g | 37.5 g |
| BA** | 25 g |  |  |
| $K_2S_2O_8$ | 0.6 g | 0.6 g | 0.6 g |
| Water | 50 g | 50 g | 50 g |
| % Solid | 22.4% | 22.7% | 22.2% |
| Particle Size | 98 nm | 93 nm | 50 nm |
| $T_g$*** | 373° K. | 378° K. | 292° K. |

*Methylmethacrylate
**Butylacrylate
***Glass Transition Temperature

EXAMPLES 28–30

Polymer blends of Examples 28, 29 and 30 were prepared by mixing 48.5 grams of polymer latex of examples 25, 26 or 27 respectively with 98.2 grams of 16.5 wt % Amphomer LV 71 solution at room temperature for 15 to 20 minutes. The Amphomer solution was prepared by dissolving 80 grams of Amphomer LV 71 (ex National Starch & Chemical Company) into a mixture of 41 0.4 grams of deionized water and 9.6 grams of aminomethylpropanol at 75° C.

EXAMPLES 31–36

Polymer latexes or polymer blends of examples 25 to 30 were formulated in a water-based hair spray pump formula with the composition shown in Table XII. All these formulas contained 5.5 wt % polymer solid. Properties and performance of these hair spray formulas were evaluated and also summarized in Table XII. The data clearly shows that only the polymer of this invention (example 30: a polymer blend of water soluble polymer and a polymer latex with a $T_g$ less than 300° K.) performed well for hair spray application. Polymer latexes alone (examples 25, 26 and 27) or the polymer blends containing polymer latex with a $T_g$ higher than 300° K. (examples of 28 and 29) were not suitable for the application because of their poor overall film properties.

TABLE XII

Formulation and Performance of Pump Hair Spray

|  | EXAMPLE |  |  |  |  |  |
|---|---|---|---|---|---|---|
|  | 31 | 32 | 33 | 34 | 35 | 36 |
| D.I. Water | 74.57 | 72.67 | 74.57 | 69.38 | 68.17 | 69.02 |
| Polymer | Ex. 25 | Ex. 26 | Ex. 27 | Ex. 28 | Ex. 29 | Ex. 30 |
|  | 24.70 | 26.60 | 24.70 | 29.89 | 31.10 | 30.25 |
| DC190 (Silicone Surfactant) | 0.10 | 0.10 | 0.10 | 0.10 | 0.10 | 0.10 |
| Methyl Paraben | 0.20 | 0.20 | 0.20 | 0.20 | 0.20 | 0.20 |
| Glydant | 0.05 | 0.05 | 0.05 | 0.05 | 0.05 | 0.05 |
| Triton X100 | 0.20 | 0.20 | 0.20 | 0.20 | 0.20 | 0.20 |
| Cetearyl Octanoate | 0.03 | 0.03 | 0.03 | 0.03 | 0.03 | 0.03 |
| Fragrance | 0.15 | 0.15 | 0.15 | 0.15 | 0.15 | 0.15 |
| TOTAL | 100% | 100% | 100% | 100% | 100% | 100% |
| Performance |  |  |  |  |  |  |
| Film Properties | Poor | Poor | Poor | Poor | Poor | Good |
| Gloss/Shine | Cloudy | Cloudy | Cloudy | Cloudy | Clear | Clear |
| Hold | Poor | Poor | Poor | Poor | Poor | Good |

TABLE XII-continued

Formulation and Performance of Pump Hair Spray

|  | EXAMPLE |  |  |  |  |  |
|---|---|---|---|---|---|---|
|  | 31 | 32 | 33 | 34 | 35 | 36 |
| Capacity Spray Characteristics | — | — | — | — | — | Good |

EXAMPLES 37–40

Two polymer latexes of examples 37 and 38 with the composition shown in Table XIII were prepared the same way as Example 25. Examples 39 and 40 were then prepared by mixing at room temperature 44.8 grams of examples 37 or 38, respectively, with 91.7 grams of Amphomer LV 71 solution, which was described in Examples 28–30.

TABLE XIII

Latex Composition of Examples 37 and 38

|  | EXAMPLE 37 | EXAMPLE 38 |
|---|---|---|
| D.I. Water | 200 g | 200 g |
| Igepal CO-880 | 12.5 g | 12.5 g |
| NaLS | 0.5 g | 0.5 g |
| Monomer |  |  |
| BA | 37.5 g | 43.8 g |
| MMA | 25.0 g | 18.7 g |
| D.I. Water | 50.0 g | 50.0 g |
| $K_2S_2O_8$ | 0.6 g | 0.6 g |
| % Solid | 22.7% | 22.6% |
| Particle size | 57 nm | 50 nm |
| $T_g$ | 262° K. | 249° K. |

EXAMPLES 41–43

Polymer blends of examples 39, 40 and 29 were formulated in a water based hair spray aerosol formula with the compositions shown in Table XIV. Properties and performance of these aerosol hair spray formulas were evaluated and also summarized in Table XIV. Performance results indicate that the polymer blend (example 39) which contained the polymer latex with a $T_g$ in the range of this invention had a very good performance for this application. The other two polymer blends containing polymer latex with a $T_g$ either higher or lower than 250°–300° K. ($T_g$ according to this invention) were not suitable for this application.

TABLE XIV

Formulation and Performance Of Water-Based Aerosol Hair Spray

|  | EXAMPLE 41 | EXAMPLE 42 | EXAMPLE 43 |
|---|---|---|---|
| D.I. Water | 39.5 | 39.5 | 38.5 |
| Polymer | Example 39 | Example 40 | Example 29 |
|  | 30.10 | 30.10 | 31.10 |
| DC 190 (Silicone Surfactant) | 0.07 | 0.07 | 0.07 |
| Triton X100 | 0.21 | 0.21 | 0.21 |
| Cetearyl Octanoate | 0.02 | 0.02 | 0.02 |
| Fragrance | 0.10 | 0.10 | 0.10 |
| Dimethylether | 30.0 | 30.0 | 30.0 |
| Performance |  |  |  |
| Film Properties | Hard | — | — |
| Gloss/Shine | Clear | Cloudy | Hazy |
| Hold Strength | Very Good | Poor | Poor |
| Spray Characteristics | Very Good | Very Good | Good |

The foregoing description and Examples illustrate selected embodiments of the present invention. In light thereof, various modifications will be suggested to one skilled in the art, all of which are within the spirit and purview of this invention.

What is claimed is:

1. An aqueous hairspray composition comprising:
   (i) a water-soluble polymer having a solution viscosity at 10% in water of less than about 20,000 cps at 25° C., the polymer being selected from the group consisting of nonionic, anionic, cationic and amphoteric hair fixatives; and
   (ii) a latex of water-insoluble polymeric particles dispersed in water, the average particle size being no larger than about 3 microns, the particles having a glass transition temperature from 250° to 300° K. and being formed of monomers selected from the group consisting of styrene, α-methylstyrene, divinylbenzene, $C_1$–$C_{20}$ ester of acrylic acid, methacrylic acid, methylmethacrylate, acrylamide, methacrylamide, crotonic acid, maleic acid, vinyl acetate, vinyl neodecanoate and combinations thereof, and the water-soluble polymer to latex particles being present in a weight ratio ranging from about 10:1 to about 1:10.

2. A composition according to claim 1 wherein the viscosity of the water-soluble polymer is less than about 15,000 cps.

3. A composition according to claim 1 wherein the average particle size is no larger than 1 micron.

4. A composition according to claim 1 wherein the water-soluble polymer is amphoteric.

5. A composition according to claim 1 wherein the water-insoluble polymeric particles are formed from respective monomers by emulsion polymerization.

6. A composition according to claim 1 wherein the concentration of water-soluble polymer ranges from about 1 to about 30% by weight.

7. A composition according to claim 1 wherein the concentration of water-soluble polymer ranges from about 1.5 to about 10% by weight.

8. A composition according to claim 1 wherein the concentration of water-insoluble polymeric particles ranges from about 1 to about 30% by weight.

9. A composition according to claim 1 wherein the concentration of water-insoluble polymeric particles ranges from about 1.5 to about 10% by weight.

10. A composition according to claim 1 wherein the ratio of water-soluble polymer to latex particles ranges from about 2:1 to about 1:2.

11. A composition according to claim 1 wherein the latex is selected from the group consisting of styrene/butyl acrylate, methyl methacrylate/butyl acrylate, vinyl acetate/butyl acrylate, vinyl acetate/methyl methacrylate and combinations thereof.

12. A method for setting hair comprising contacting the hair with an aqueous hairspray composition comprising:
   (i) a water-soluble polymer having a solution viscosity at 10% in water of less than about 20,000 cps at 25° C., the polymer being selected from the group consisting of nonionic, anionic, cationic and amphoteric hair fixatives; and
   (ii) a latex of water-insoluble polymeric particles dispersed in water, the average particle size being no larger than about 3 microns, the particles having a glass transition temperature from 250° to 300° K. and being formed of monomers selected from the group consisting of styrene, α-methylstyrene, divinylbenzene, $C_1$–$C_{20}$ ester of acrylic acid, methacrylic acid, methylmethacrylate acrylamide, methacrylamide, crotonic acid, maleic acid, vinyl acetate, vinyl neodecanoate and combinations thereof, and the water-soluble polymer to latex particles being present in a weight ratio ranging from about 10:1 to about 1:10.

* * * * *